(12) United States Patent
Landau (10) Patent No.: US 6,648,850 B2
(45) Date of Patent: Nov. 18, 2003

(54) DURABLE NEEDLE-LESS JET INJECTOR APPARATUS AND METHOD

(75) Inventor: Sergio Landau, Laguna Nigel, CA (US)

(73) Assignee: Bioject, Inc., Portland, OR (US)

( * ) Notice: Subject to any disclaimer, the term of this patent is extended or adjusted under 35 U.S.C. 154(b) by 24 days.

(21) Appl. No.: 09/877,911

(22) Filed: Jun. 8, 2001

(65) Prior Publication Data

US 2002/0188249 A1 Dec. 12, 2002

(51) Int. Cl.$^7$ .............................................. A61M 5/30
(52) U.S. Cl. .......................... 604/70; 604/68; 604/181; 604/207
(58) Field of Search .............................. 604/68–72, 136, 604/140–145, 181–187, 207–211, 246

(56) References Cited

U.S. PATENT DOCUMENTS 5,383,851 A * 1/1995 McKinnon et al. ........... 604/68
6,080,130 A * 6/2000 Castellano ................... 604/68
6,168,587 B1 * 1/2001 Bellhouse et al. .......... 604/191
6,406,455 B1 * 6/2002 Willis et al. ................ 604/191

\* cited by examiner

Primary Examiner—Gregory L. Huson
Assistant Examiner—Amanda Flynn
(74) Attorney, Agent, or Firm—Kolisch Hartwell, P.C.

(57) ABSTRACT

A gas-powered, durable, needle-less hypodermic jet injection device (10, 110) includes a hand-held injector (12, 112) which provides a volume of liquid medication to be injected, an injection orifice, and an injection piston. Forceful movement of the injection piston causes an injection jet of medication to be expelled from the injection orifice. The injection device also includes a hermetically sealed gas pressure cartridge (28) which is opened in preparation to effecting a jet injection, and which powers the jet injection, but from which pressurized gas is not allowed to flow in volume until a user of the device shifts a valving spool (24).

32 Claims, 5 Drawing Sheets

DURABLE NEEDLE-LESS JET INJECTOR APPARATUS AND METHOD

BACKGROUND OF THE INVENTION

1. Field of the Invention

The present invention relates generally to a durable, multiple-use needle-less (or needle-free) jet injection device and methods of its making, operation, and use. Particularly, this invention relates to a durable gas-powered, rechargeable, hypodermic jet injection device which comprises a hand-held injector having a refillable drug cartridge carrying injectable medication, a sealed cylinder of pressurized gas, a mechanism for penetrating the gas cylinder preparatory to effecting an injection, and a trigger device for releasing gas from the gas cylinder in order to effect an injection by action of the pressurized gas on an injection piston

2. Related Technology

Needle-less or needle-free hypodermic jet injection devices have been in commercial use for over 40 years. A number of these devices have used pressurized gas to power a hypodermic jet injection. The related technology includes a number of teachings for gas-powered injection devices, including: U.S. Pat. No. 4,596,556, issued Jun. 24, 1986 to J. Thomas Morrow, et al.; U.S. Pat. No. 4,913,699; issued Apr. 3, 1990 to James S. Parsons; and U.S. Pat. No. 5,730,723, issued Mar. 24, 1998, to Thomas P. Castellano, et al. WIPO publication WO 97/37705 also discloses a gas powered disposable needle-less hypodermic jet injector.

The Morrow, et. al. '556 patent is believed to teach a reusable hypodermic jet injection device in which a housing receives a shell or cartridge having a bore leading to a discharge aperture. Within the bore is received both a plunger sealingly engaging the bore, and a pressurized gas cylinder which rests against the plunger. The injection device includes a ram which has a penetrating tip confronting a penetrable wall section and seal of the gas cylinder, and a discharge mechanism for driving the ram through the penetrable wall section of the gas cylinder when a trigger device is released. Discharge of the pressurized gas from the cylinder drives the plunger to effect a jet injection, and also drives the seal of the gas cylinder to effect resetting of the discharge mechanism. The shell with its plunger, and spent gas cylinder, is discarded after an injection; and a new shell pre-filled with medication and with a new gas cylinder is used for each injection.

The Parsons '699 patent is believed to teach a single-use jet injector which is totally discarded after one use. This injector is believed to have a body with a pair of gas chambers separated by a breakable valve. One of the gas chambers contains a pressurized gas, while the other chamber is sealingly bounded by a piston which drives a plunger. The plunger sealingly bounds a chamber into which a dose of medication is loaded by the user before the injection. This medication dose chamber leads to an injection orifice so that when the valve is broken, the piston and plunger are moved by pressurized gas communicated to the second chamber, and the plunger drives the medication forcefully out of the injection orifice to form an injection jet. After a single use, the device is discarded.

The Castellano '723 patent, which was issued in 1998 and which does not cite the earlier Parsons '699 patent, is believed to teach substantially the same subject matter as Parsons et al.

WIPO publication WO 97/37705 published pursuant to a Patent Cooperation Treaty (PCT) application for joint inventors Terence Weston and Pixey Thomlea, is believed to disclose a disposable hypodermic jet injector in which the device is powered by a gas pressure spring of the type common in the tool and die art as a substitute for the conventional metal spring-powered ejector pin. In the Weston device, the ram of the gas pressure spring is held in a contracted position by a trigger mechanism. When the trigger mechanism is released, the gas pressure spring is supposed to expand and drive a piston sealingly received in a bore and leading to a fine-dimension orifice in order to produce a jet hypodermic injection from liquid held in the bore ahead of the piston.

The Weston device is thought to have several deficiencies: such as difficult and costly manufacturing and sterilization processes, because pressurized gas and a drug dose need to be contained in the same package; and including a possible inability to endure long-term storage while still retaining the gas pressure in the gas spring to power an injection, and also maintaining the medication integrity. In other words, the gas pressure spring of the Weston device contains only a small quantity of gas, and depends upon the sealing relationship of the ram of this spring with a cylinder within which the ram is movably and sealingly received in order to retain this gas pressure. Even a small amount of gas leakage over time will be enough to render this injector inoperative.

SUMMARY OF THE INVENTION

In view of the above, it is desirable and is an object for this invention to provide a needle-less jet injection device which reduces the severity of or avoids one or more of the limitations of the conventional technology.

Thus, it is an object of this invention to provide a durable, needle-free gas-powered jet injector utilizing a pressurized gas source which is hermetically sealed until it is opened in preparation for effecting the jet injection.

This jet injector includes a unique valving mechanism in one operative position containing the pressurized gas communicating from the opened gas source, until the valving mechanism is moved to a second operative position communicating the pressurized gas to an injection piston.

Further, an object of this invention is to provide such a jet injector in which the device is particularly efficient and elegant with respect to the design, functionality, and materials utilization of the components of the device. In other words, the parts count of the device is small, and materials are utilized which ease and reduce the cost of manufacture of the device. Nevertheless, because of the unique design of the device, inexpensive materials of relatively low strength are able to serve well. For example, the valving device may be made of injection molded plastic, and yet contain pressures of over 1000 PSI in preparation for a jet injection.

Accordingly, an embodiment of the present invention provides a jet injection device comprising: a device body having a forward end; an injection cylinder carried at the forward end of said device body and having a cylinder bore in which an injection piston is movable to cooperatively define a variable-volume chamber for holding a dose of liquid medication; a fine-dimension injection orifice in liquid flow communication with said variable-volume chamber to receive liquid medication and discharge this medication as a high velocity forceful jet for jet injection of medication upon forceful movement of said injection piston in said cylinder; a power source in said device body for forcefully moving said piston in said cylinder in response to communication of gas pressure to a gas pressure piston, a source of gas pressure; and a trigger assembly for effecting communication of pressurized gas from said source to said gas pressure piston, said trigger assembly including a stem member with a pair of ports spaced axially apart, and a pair of axially spaced apart seal members movable along said stem from a first position in which said seal members bracket only a single one of said axially spaced apart ports, said trigger assembly being manually movable axially to a second position in which said pair of seal members bracket both of said pair of axially spaced ports to communicate pressurized gas from one of said pair of ports to the other of said pair of ports and to said gas pressure piston.

According to a further aspect this invention provides: a method of providing a jet injection device, said method comprising steps of: providing a device body having a forward end; providing an injection cylinder, and carrying said injection cylinder at a forward end of said device body, providing said injection cylinder with a cylinder bore in which an injection piston is movable to cooperatively define a variable-volume chamber for holding a dose of liquid medication; providing a fine-dimension injection orifice in liquid flow communication with said variable-volume chamber to receive liquid medication, and discharging the liquid medication as a high velocity forceful jet for jet injection of medication upon forceful movement of said injection piston in said cylinder; providing a power source in said device body for forcefully moving said injection piston in said cylinder in response to communication of gas pressure to a gas pressure piston, providing a source of gas pressure; and providing a trigger assembly for effecting communication of pressurized gas from said source to said gas pressure piston, configuring said trigger assembly to include a stem member with a pair of ports spaced axially apart, and providing a pair of axially spaced apart seal members movable along said stem from a first position in which said seal members bracket only a single one of said axially spaced apart ports, providing for said trigger assembly to be manually movable axially to a second position in which said pair of seal members bracket both of said pair of axially spaced ports to communicate pressurized gas from one of said pair of ports to the other of said pair of ports and to said gas pressure piston.

Additional objects and advantages of this invention will appear from a reading of the following detailed description of two exemplary preferred embodiments of the invention, taken in conjunction with the appended drawing Figures, in which the same reference numeral is used throughout the several views to indicate the same feature, or features which are analogous in structure or function.

DETAILED DESCRIPTION OF EXEMPLARY PREFERRED EMBODIMENTS OF THE INVENTION

Overview of the Injection Device and its Use

Figure 1:
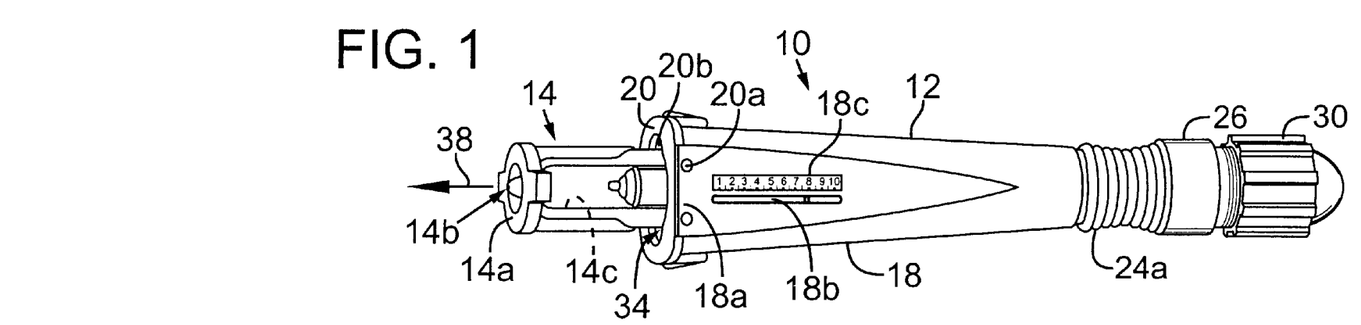
FIG. 1 provides an exterior side elevation view of a durable, needle-less jet injector device embodying the present invention.
Figures 1A, 2:
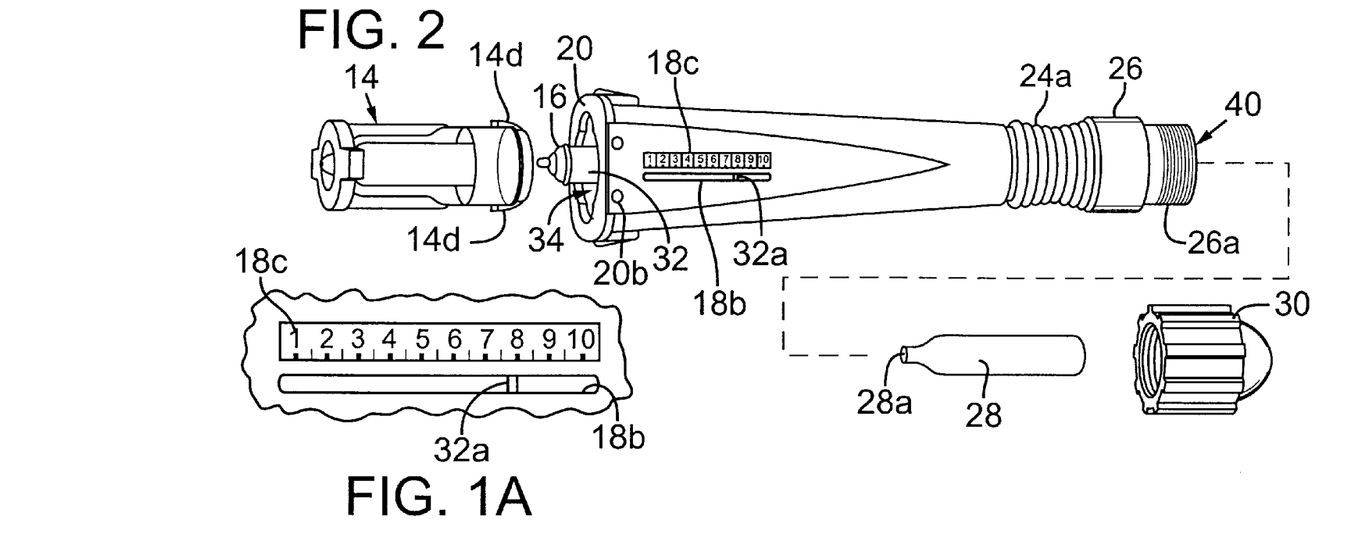
FIG. 1a is a fragmentary view of a portion of the device seen in FIG. 1, illustrating a measuring scale feature of the device.
FIG. 2 is an exterior side elevation view of the injector device seen in FIG. 1, but shows the device partially disassembled with an injection cartridge, a pressurized gas cylinder and a cap of the device removed from their normal operative positions.

Viewing FIGS. 1, 1a, and 2 in conjunction with one another, a needle-free, jet injection device 10 is illustrated. This device 10 includes a multi-piece body 12, including a removable injection cylinder member 14, having an injection piston 16 sealingly and movably received therein, a forward body section 18 carrying a trigger sleeve 24, an aft body section 26 receiving a pressurized gas cartridge 28, and a cap member 30 which is threadably engageable onto the aft body section, as will be further explained below.

The body 12 is preferably fabricated principally of plastic polymers, and may be injection molded for economy of manufacture, although the invention is not so limited. As is seen in FIG. 2, the injection cylinder 14 is removably attached to the forward body section 18. Similarly, the injection piston 16 is removably attached to a reciprocable ram member 32, which is reciprocable in the forward body section 18. Thus, it is to be understood that the injection cylinder 14 and injection piston 16 are capable of being used more than once to effect a hypodermic jet injection to a particular individual, but may be used only once if desired, and may be disposed of when the user is finished using a particular cylinder 14 and piston 16.

When a user is finished using a particular set of injection cylinder 14 and injection piston 16, these are then removed from the device 10, are disposed of properly, and a new injection cylinder 14 and injection piston 16 are installed on the device, as will be explained below. It will be seen that the injection piston 16 is installed onto the ram 32 by pushing the injection piston member 16 at a recess 16a thereof onto a protruding stem portion (further described below) of the ram member 32. The injection piston 16 "snaps" into place on the ram 32. Then, the user simply places the injection cylinder 14 over the injection piston 16, and pushes the injection cylinder 14 axially into an axial opening 34 of the forward body section 18.

A user of the device 10 then prepares the device to effect an injection by attaching a medicine vial to the end of the injection cylinder 14, and utilizes a protruding thumb wheel 36 on the body portion 18 to effect rearward movement of the ram 32 and injection piston 16. This rearward movement of the piston 16 causes medication to be drawn into the injection cylinder 14. It will be noted that the word "medication," or the word "drug," as used herein are intended to encompass, for example, and without limitation, any medication, pharmaceutical, therapeutic, vaccine, or other material which can be administered by jet injection. Essentially, such an injectable medication or drug is in the form of a substantially incompressible liquid, and as will be seen, this liquid substantially fills the drug injection cartridge 14 so that no ullage volume of compressible gas is present in this cartridge (i.e., between the cylinder 14 and piston 16).

It will be noted that the drug injection cylinder 14 has an end surface 14a at which is defined a fine-dimension injection orifice opening 14b. The injection piston 16 is sealingly and movably received into a larger diameter bore 14c of the cylinder 14. And, the cylinder 14 includes a pair of radially outwardly extending and axially tapering latching lugs 14d. When the device 10 is used to effect an injection, a high velocity jet of liquid medication issues from this orifice (as is indicated by arrow 38 of FIG. 1). To use the device 10, the user fills the injection cylinder as explained above, and then places the gas cartridge 28 into a recess 40 at the aft end of aft body section 26. The cap 30 is then threaded forcefully onto the aft body section, opening the gas cartridge and communicating gas pressure to a valved chamber (to be further explained) controlled by the trigger sleeve 24. The end surface 14a is pressed against the skin of a patient who is to receive the jet injection, and then the device 10 is triggered by forward movement of the trigger sleeve 24 so that the jet 38 issues out of orifice 14b and penetrates the patient's skin. Thus, the liquid medication enters the tissues of the patient without the use of a hypodermic needle.

Structure of the Device 10

Figure 3:
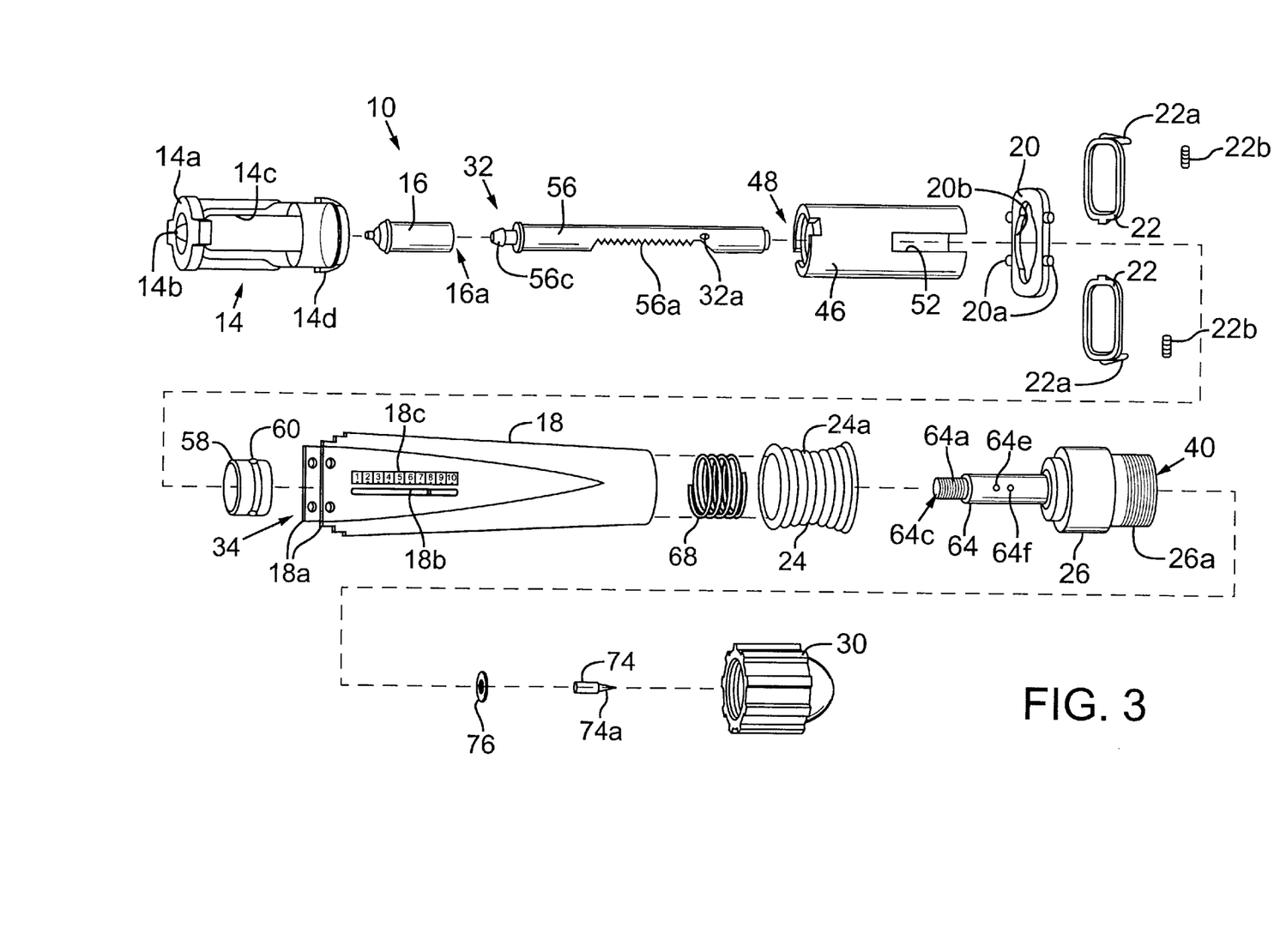
FIG. 3 provides an exploded assembly view of the device, with its component parts arrayed in perspective for ease of viewing.
Figure 4:
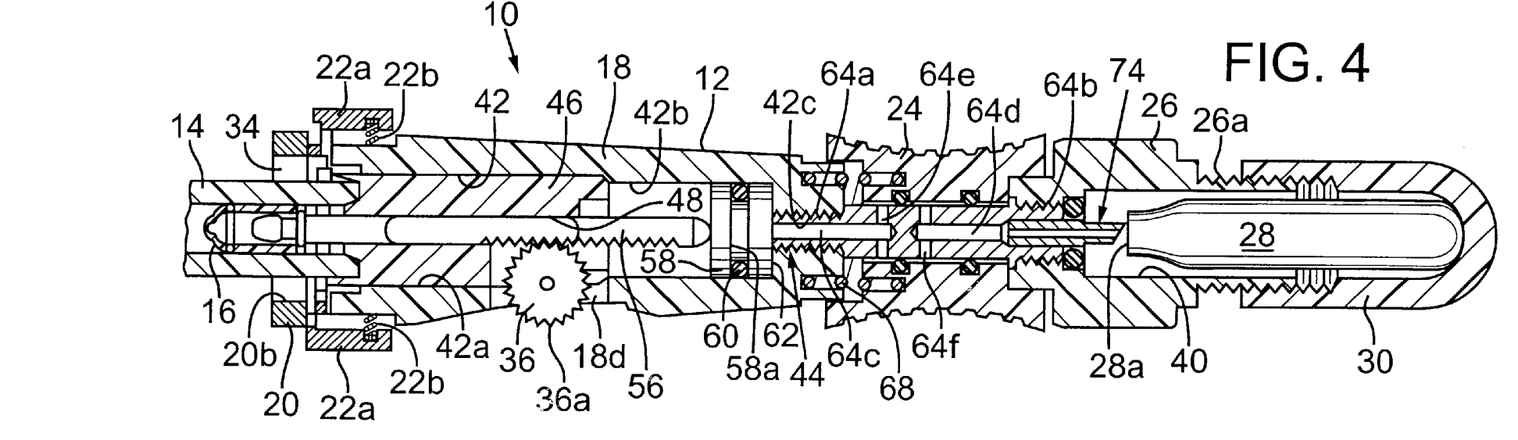
FIG. 4 is a fragmentary cross sectional taken longitudinally of the device seen in FIG. 1, and shows the jet injection device in a preparatory configuration.
Figure 4A:
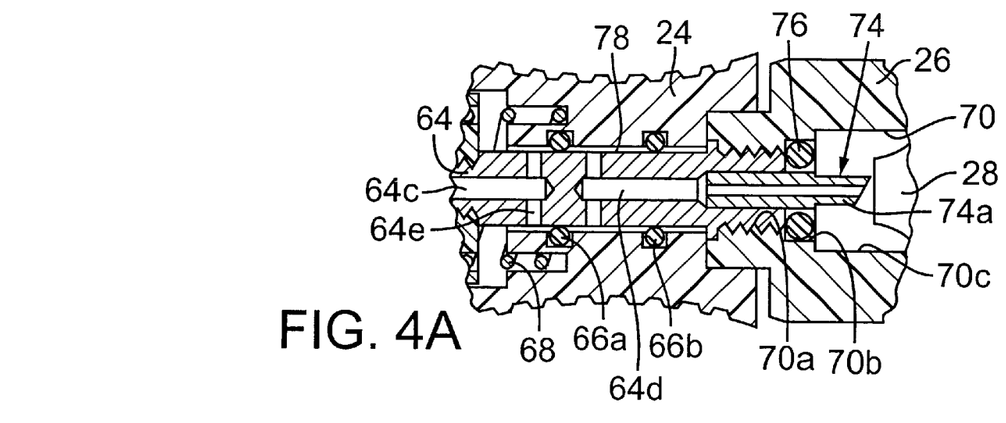
FIG. 4a is a fragmentary cross sectional view similar to a portion of FIG. 4, and shows the jet injection device in a ready configuration.

Turning now to FIGS. 3, 4, and 4a, in conjunction with one another, FIG. 3 shows an exploded perspective view of the component parts of the device 10. In FIG. 4 the device 10 is shown in longitudinal cross section preparatory to administering an injection. In FIG. 4a is shown a fragmentary cross sectional portion of the device at the trigger sleeve 24, with the device in a preparatory configuration before the beginning of the injection. The forward body portion 18 defines a stepped through bore 42 (best seen in FIG. 4) having a larger diameter portion 42a which extends from the forward end (i.e., the left end as seen in FIG. 4) toward the aft end of the body portion 18 and device 10. At the forward end of the body portion 18 this body defines a pair of laterally spaced apart flanges 18a, and a metallic plate member 20 is received between these flanges and is secured by a pair of pins 20a on each side penetrating the respective flange 18a and securing into an edge of the plate member 20. The plate member 20 defines a "key hole" opening 20b, which is configured to pass the cylindrical body of the injection cylinder 14, as well as the pair of latching lugs 14d. Thus, the user of the device pushes the aft end of the cylinder 14 (and latching lugs 14d) through the plate member 20 and into a recess at the forward end of bore 42. Nested behind the metal plate member 20 is a cooperating pair of latching plates 22. Each latching plate 22 includes a respective outwardly disposed and longitudinally extending finger pad portion 22a. Each finger pad portion 22a receives a small coil spring 22b, which biases the respective latching plate radially outwardly at its finger pad end. Thus, each one of the latching plates 22 partially obstructs a portion of the "key hole" opening 20b opposite to the finger pad 22a of that latching plate. When a user pushes the aft end of a cylinder 14 (and latching lugs 14d) into and slightly past the plate 20, the latching plates 22 separate slightly against the bias provided by springs 22b, and then latch behind the latching lugs 14d. Thus, the injection cylinder 14 is securely attached onto the forward end of the body 18. The user may remove the injection cylinder 14 from the body portion 18 by pushing inwardly on the finger pads 22a.

An elongate window slot 18b opens from bore portion 42a outwardly on the body portion 18, and is seen in FIGS. 1 and 2. Particularly, this window slot 18b is seen in FIG. 1a having a volume measurement scale 18c disposed on the body portion 18 adjacent to this window slot 18b. Another slot 18d opens from the bore portion 42a outwardly on the body portion 18 and rotationally accepts the thumb wheel 36. It will be noted that the thumb wheel 36 is formed as a pinion gear, and has gear teeth 36a continuously around its circumference. Thus, when the user of the device 10 manually rotates wheel to move ram 32, an indicator 32a carried by this ram moves relative to scale 18c, and is visible at window 18b.

Bore portion 42a of the body portion 18 communicates with a second bore portion 42b of slightly smaller diameter, and bore portion 42b communicates with a bore portion 42c opening rightwardly on the body portion 18. In the bore portion 42c screw threads 44 are formed, as is best seen in FIG. 4. Retained in bore portion 42a is a bushing member 44. This bushing member 44 defines a cylindrical though bore 48, and two side openings 50 and 52. The one side opening 50 is congruent with window slot 18b, while the side opening 52 extends from the aft end of bushing member 44 partially toward the forward end of this bushing member, and accepts the thumb wheel 36. As is seen in FIG. 4, the thumb wheel 36 is rotationally received on a pin 54 which is press fitted into a matching bore in the body portion 18. The pin 54 intrudes on bore portion 42a so that the drilling of the bore for pin 54 while the bushing member 44 is present in the bore portion 42a provides a matching groove (not seen in the drawing Figures) on the outer surface of this bushing member. Thus, when the bushing is placed into bore portion 42a, and thumb wheel 36 is placed in slot 18d and side opening 52, the press fitting of the pin 54 into its bore also retains the thumb wheel 36, and retains bushing member 44 in the bore portion 42a.

Slidably received in the bore 48 of bushing member 44 is a ram/rack member 56 (hereinafter referred to as a "ram" member). This ram member 56 at a forward portion thereof defines the ram 32, and further defines a gear rack section 56a along its side. Importantly, the gear rack section 56a does not extend to either end of the ram member 56, so that once the ram member 56 is installed into bushing 44, and the thumb wheel 36 is meshed at its gear teeth 36a with the gear rack section 56a, then the ram member 56 is permanently retained in the bushing 44. The ram 56 defines an end surface 56b disposed toward the aft end of the device 10, and an opposite stem portion 56c of reduced diameter and having conical surfaces tapering in each axial direction.

Movably and sealingly received into the bore portion 42b, and engaging against end surface 56b of the ram member 56 is a gas piston member 58. This gas piston member 58 defines a groove 58a in which is carried an O-ring type of sealing member 60. Accordingly, the body portion 18 and gas piston member 58 cooperatively define a variable volume chamber 62 (best seen in FIG. 5a). Threadably and sealingly received into the bore portion 42c is a threaded end part 64a of a valving stem 64. This valving stem has an opposite threaded end part 64b, and a pair of opposite axially extending bores 64c and 64d each opening on an opposite end surface of the stem member 64, and extending toward but short of one another. Each of the axially extending bores 64c and 64d is communicated outwardly onto the outside surface of the stem 64 by a respective one of a pair of axially spaced apart apertures, which in a preferred embodiment comprises cross bores 64e and 64f.

Slidably carried on the stem member 64 is the trigger sleeve 24, which serves as a spool valve relative to the cross bores 64e and 64f. According to this illustrated preferred embodiment of the device, the trigger sleeve member 24 carries a pair of axially spaced apart O-ring seal members 66a and 66b. In a first position of the trigger sleeve member (as is seen in FIGS. 4 and 4a) the O-rings 66a and 66b bracket the one cross bore 64f. A coil spring 68 extends between the body portion 18 and the trigger sleeve 24 to yieldably bias this trigger sleeve 24 to the first position seen in FIGS. 4 and 4a. The trigger sleeve member 24 defines a grooved, knurled, or otherwise textured manual engagement surface 24a. Further, those ordinarily skilled in the pertinent arts will appreciate that the invention is not limited to having the trigger sleeve member 24 carry O-ring sealing elements, like seal members 66a and 66b. That is, the sleeve member 24 may carry a different kind of sealing device or ring, or the sleeve member 24 may itself integrally define a pair of axially spaced apart sealing bands or elements which sealingly and slidably engage the stem member 64.

Threadably and sealingly received onto the threaded end part 64b of the stem member 64 is the aft body section 26. This aft body section 26 defines a stepped through bore 70 having a large diameter bore section 70a, a counter bore section 70b, and a smaller diameter bore section 70c opening forwardly on the section 26. The smaller diameter bore section 70c defines a screw thread 72 which is engaged by the stem member 64. The stem member 64 carries a tubular penetrator member 74 having a sharp spike portion 74a projecting into the bore section 64a. In the counter bore 64b is received a small O-ring seal member 76.

Received into the bore section 64b is the gas cartridge 28, which in the position of the component parts seen in FIG. 4, is not penetrated by the spike 74a. That is, a penetrable diaphragm portion 28a of the gas cartridge 28 seals pressurized gas therein. Further, the aft body section 26 defines a thread section 26a, and the cap member 30 is threadably received upon this thread section 26a. Viewing FIG. 4a, it is seen that in the first position of the trigger spool, pressurized gas communicating along the bore 64d can communicate along cross bore 64f to an annular chamber 78 within the trigger sleeve 24. However, the pressurized gas in chamber 78 cannot communicate to cross bore 64e, or to bore 64c and chamber 62.

Figure 5:
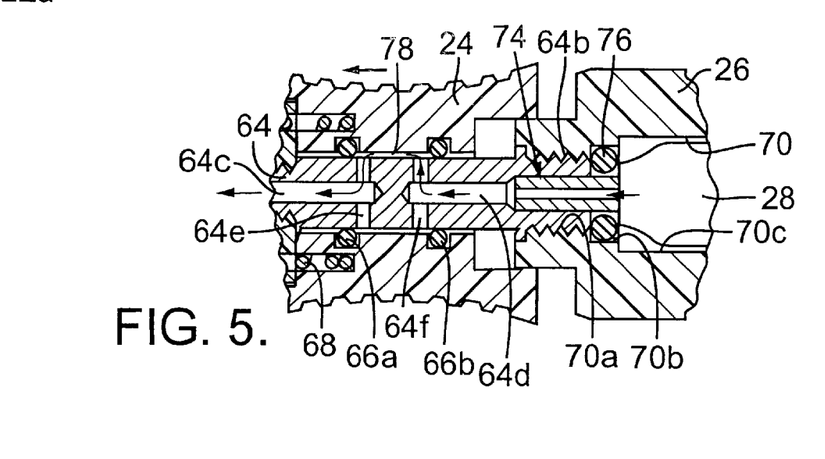
FIG. 5 is also a fragmentary cross sectional view similar to FIGS. 4 and 4a, but shows the jet injection device at the beginning of and during the process of effecting a jet injection.

Now turning to FIG. 5 it is seen that when a user of the device winds the cap member 30 tightly onto the aft body section 26, the gas cartridge 28 is impaled onto the spike 74a, and pressurized gas communicates to annular chamber 78. However, an injection does not result because the pressurized gas is contained at chamber 78. In this respect it will be appreciated that although the trigger sleeve 24 may be made of plastic polymers and although the gas pressure from cartridge 28 may be about 1000 PSI, or higher, the gas pressure in chamber 78 does not have much surface area to act upon. That is, the stem 64 is preferably about 0.220 inch in diameter at the O-ring sealing members 66a and 66b. Thus, the plastic material of the trigger sleeve 24 is adequate to withstand the pressure force created at the chamber 78. In order to effect an jet injection with the device 10, the user fills the injection cylinder 14 with medication (as was described above), and tightens the cap 30 onto the aft end of the body section 26 in order to penetrate a fresh gas cartridge. The user then places the device 10 at surface 14a against the skin at the desired injection site. By holding the device 10 in the fingers, a thumb and index finger (for example) may be utilized on the trigger sleeve so that after the device is pressed to the skin, this trigger sleeve is slid forward to the position seen in FIG. 5a.

Figure 5A:
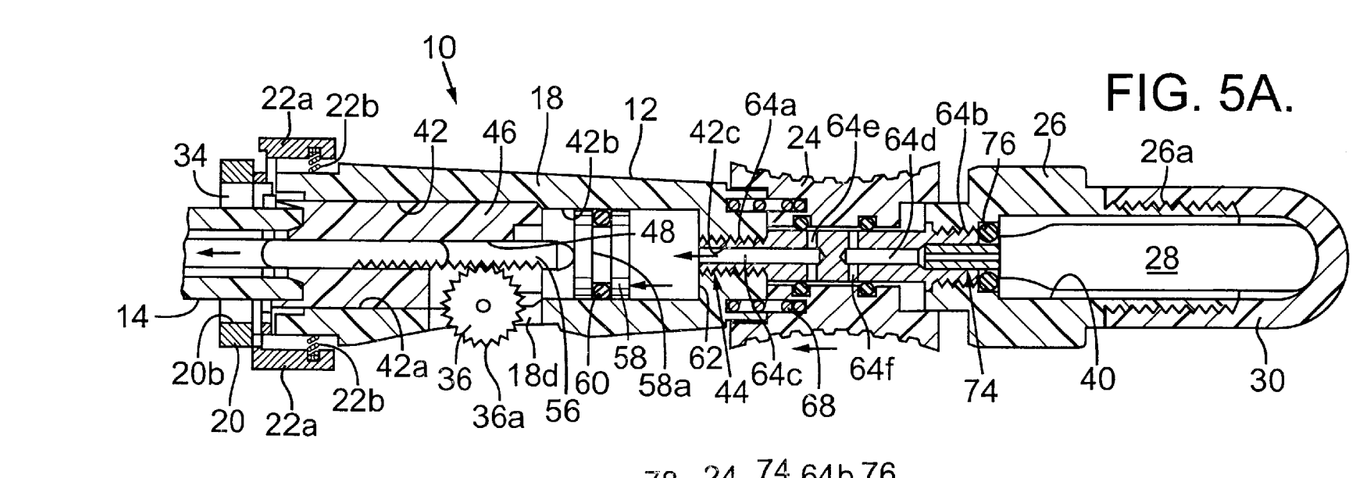
FIG. 5a is a full longitudinal fragmentary cross sectional view similar to FIG. 5, and shows the jet injection device during the process of effecting a jet injection.

FIG. 5a shows the device 10 immediately after the trigger sleeve 24 is slid forward to a second position by a user of the device as described above. The trigger sleeve 24 slides forward against the bias of the spring 68 and against the friction of the two O-ring seals 66a and 66b to the second position seen in FIG. 5a. In this second position for the trigger sleeve, the pair of O-ring seals 66a and 66b bracket the pair of cross bores 64e and 64f. That is, the chamber 78 now communicates with both cross bores 64e and 64f so that pressurized gas flows from the cartridge 28 through the penetrator 74, along bore 64d, radially out cross bore 64f, along axial chamber 78 to cross bore 64e, and from the cross bore 64e along bore 64c to the chamber 62 in the forward body portion 18. The pressurized gas in chamber 62 drives gas piston 58 forcefully forward, driving ram 56 forcefully forward.

Recalling the description above, it is understood that the ram 56 carries the injection piston 16 within injection cylinder member 14. As the injection piston 16 is forced forward, it drives liquid medication from the cylinder 14 via orifice 14b, forming very high velocity injection jet 38 (recalling FIG. 1). This injection jet 38 penetrates the patient's skin, and delivers the liquid medication to the patient without the use of a hypodermic needle.

After the injection is completed, the user removes cap 30 and disposes of the used gas cartridge 28. The user may reuse the injection cylinder 14 and injection piston 16 many times (perhaps for a month of injections, for example) so long as each and every injection is administered to the same person. At the end of the period of time for use of one injection cylinder and piston, these two items are also removed from the injection device and are replaced with a new injection piston and injection cylinder.

Figure 6:
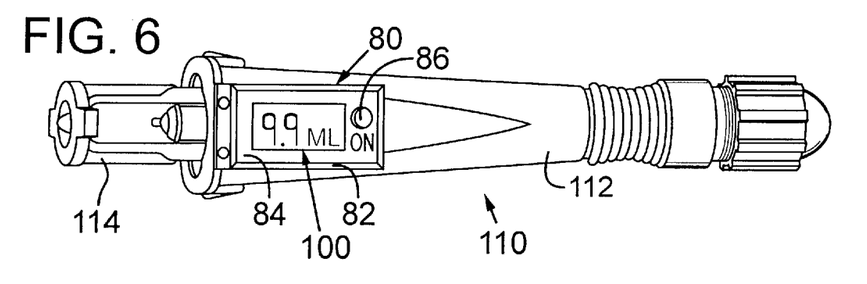
FIG. 6 is a fragmentary perspective view similar to FIG. 1, but shows an alternative embodiment of a durable, needle-less jet injection device according to the present invention.
Figure 7:
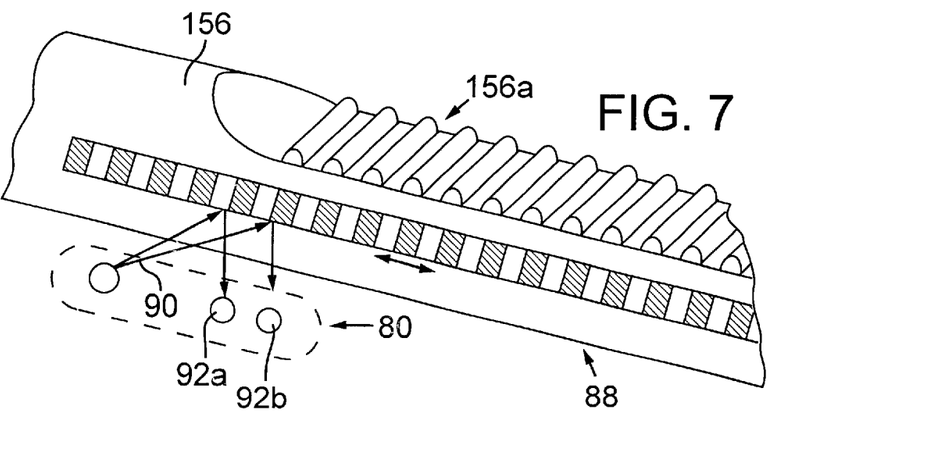
FIG. 7 is a fragmentary and somewhat schematic view of a portion of the device seen in FIG. 6, and particularly shows a measuring and indicating portion of the device.
Figure 8:
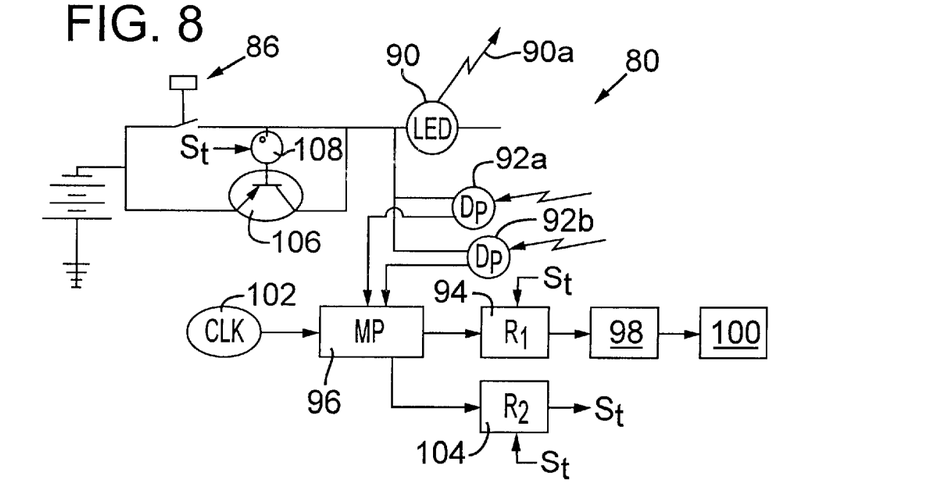
FIG. 8 provides a schematic indication of an exemplary architecture for a measuring and indicating device of the embodiment seen in FIGS. 6 and 7.

Viewing now FIGS. 6–8, an alternative embodiment of a needle-free, jet injection device is shown. Because the device illustrated in FIGS. 6–8 has many features that are the same as, or which are analogous in structure or function to those first illustrated and first described above, these features are indicated on FIGS. 6–8 using the same reference numeral used above, and increased by one-hundred (104). In fact, the embodiment of FIGS. 6–8 is so similar to that of FIGS. 1–5a that the reader may consider the embodiments the same with the exception of the additional subject matter described below for this second embodiment. Viewing now FIGS. 6 and 7 in conjunction with one another, a needle-free, jet injection device 110 is illustrated. This device 110 includes a multi-piece body 112, much like the device 10 illustrated and described above. However, rather than having a volume measurement scale 18c disposed on the body 12 and an indicator 32a movable along this scale, the embodiment of FIGS. 6 and 7 has a digital indicator 80 disposed on the forward body portion 118. This digital indicator 80 has a housing portion 82, and a display face 84. According to one embodiment of the indicator 80, on the display face 84 is presented to the user of the device two digits. One of these digits may represent "tenths" of a milliliter, while the other represents "hundredths" of a milliliter of volume in the injection cylinder 114. In this embodiment, the tenths digit preferably changes from one integer value to the next (i.e., 0, 1, 2, 3, etc.), while the hundredths digit dithers back and forth between the zero value and the 5 value. Thus, this embodiment of the indicator 80 would give indicated volume values of, for example: 0.0, 0.5, 1.0, 1.5, 2.0, 2.5, etc. According to another embodiment of the indicator which is usable with injectors having a larger volume capacity for the injection cylinder 114, the two digits of the display 80 would include one whole integer digit (i.e., from 0 to 9) and one "tenths" digit (i.e., from 0.0 to 0.9). Thus, the digital indictor 80 in this case would be capable of indicating to the user of the device 110 a volume measurement of medication contained within injection cylinder 114 of from 0.0 ml to 9.9 ml.

The indicator 80 includes a small battery (not seen in FIGS. 6 or 7—but see schematic FIG. 8) as well as a push button 86 serving as an "on" switch. No "off" switch is required for the indicator 80 because it includes a timer turning it off automatically after a selected interval of operation.

FIG. 7 illustrates in fragmentary sectional view that the present embodiment does not include an indicator 32*a* carried on the ram member 156 (as was the case with ram member 56 of the first embodiment). Instead, this second embodiment has an elongate, fine-dimension, binary scale 88 formed along the side of the ram 156. This binary scale may 88 may be formed by any one or more of several conventional means. However, one particularly preferred method is a polishing operation, followed by masking and etching operations. The polishing operation leaves a surface on the ram 156 of high reflectivity, while the masking and etching operations leave alternating fine-dimension bands of "satin" finish. The satin finished bands have a lower reflectivity than the interdigitated bands of polished surface. Thus, a binary scale of alternating bands of polished surface and satin surface is provided within the scale 88 along the length of ram 156. These alternating bands of polished and satin surface on ram 156 may each be only about a few thousands of an inch in width. Thus, as the ram 156 is moved by the thumb wheel 136, many alternating bands of polished and satin surface pass a particular stationary point on the housing 12. Further, a single milliliter of volume in the injection cylinder 114 may represent the passage of many bands past a particular point. Thus, even though the display face 84 of the present embodiment has an accuracy resolution of 0.1 ml, the actual measuring resolution of the digital indicator 80 may considerably exceed this level of accuracy if desired.

Accordingly, as is seen in FIGS. 7 and 8, the digital indicator 80 includes a small light source 90 (a light emitting diode is preferred, although the invention is not so limited). This light source casts a beam 90*a* on the ram 156, onto the binary scale 88, and more or less of the beam is reflected back toward the indicator 80 depending on whether a polished band or a satin band of surface on the binary scale 88 is most aligned with the light source. A pair of light responsive element 92*a* and 92*b* (photodiodes or phototransistors are preferred, although the invention is not so limited) are spaced apart slightly along the length of scale 88 and each responds to the level of reflected light from the binary scale 88 to each produce alternating levels of current as the bands of polished and satin surface move past during movements of the ram 156. Because the indicator 80 includes a pair of light responsive elements 92*a* and 92*b*, the direction of relative movement of the ram 156 is determined by the time phase of the alternating levels of current pulses produced first from one of the indicators 92*a* or 92*b*, and then from the second one of the elements 92*a* or 92*b*. The alternating current levels from the elements 92 are analyzed for time phase and are counted by a counter register 94, with addition or subtraction from the register total accounting for the "sign" of the counts (i.e., positive for rearward movement of the ram 156 increasing the volume in the injection cylinder, and negative for forward movement of the ram). To achieve this analysis of the time phase of the current pulses from elements 92*a* and 92*b*, a small microprocessor 96 is used which also converts this current pulse count from the elements 92*a* and 92*b* into milliliters of volume displacement (recalling that many bands of the binary scale 88, and many current pulses, may be proportional to a single milliliter of volume in the cylinder 114, with a view to the diameter of the injection piston 116 in injection cylinder 114). A display driver 98 receives a value from the count register and microprocessor 96, and presents this value in digital form on a digital display 100 of the digital indicator 80 (i.e., the display providing display face 84). The microprocessor 96 has associated with it a clock 102 for its own operation (i.e., supplying clock pulses). Accordingly, another counter register 104 accumulates these clock pulses from the moment of switch "on" of the digital indicator 80 until a predetermined clock count is reached, at which the digital indicator turns itself off by outputting a reset and shut down signal "St", thus resetting both of the count registers 94 and 104, and unlatching a power transistor 106 via momentary opening of a normally closed switch 104.

In view of the above, it is seen that the "on" switch 86 when pushed by the user latches the power transistor 106 closed until it is unlatched by the timing out of the counter register 106. Thus, the user of the device first "zeroes" the device by moving the ram 156 all the way forward, and turning on the indicator 80 by pushing button 86. The indication on display 100 thus starts at 0.0, and increases as ram 156 is moved rearward. Then, the medication is introduced into the injection cylinder 114 by retraction of the injection piston 116. This method of operation of the indicator 80 will also account for purging of air from the injection cylinder (as the count on digital display will fall and rise) as the ram 156 is dithered to purge air. When the user has filled the injection cylinder 114 with a required quantity of medication (as is indicated on the digital indicator 80), then the device is ready for use. Thereafter, the use of the device 110 to effect a jet injection is just the same as the first embodiment described above.

While the invention has been depicted and described by reference to two particularly preferred embodiments of the invention, such reference does not imply a limitation on the invention, and no such limitation is to be inferred. The invention is capable of considerable variation and alteration in its embodiments without departing from the scope of this invention. Accordingly, the invention is intended to be limited only by the spirit and scope of the appended claims, giving cognizance to equivalents in all respects.

I claim:

1. A jet injection device comprising:

a device body having a forward end;

an injection cylinder carried at the forward end of said device body and having a cylinder bore in which an injection piston is movable to cooperatively define a variable-volume chamber for holding a dose of liquid medication;

a fine-dimension injection orifice in liquid flow communication with said variable-volume chamber to receive liquid medication and discharge this medication as a high velocity forceful jet for jet injection of medication upon forceful movement of said injection piston in said cylinder;

a power source in said device body for forcefully moving said piston in said cylinder in response to communication of gas pressure to a gas pressure piston, a source of gas pressure; and a trigger assembly for effecting communication of pressurized gas from said source to said gas pressure piston, said trigger assembly including a stem member with a pair of apertures spaced axially apart, and a pair of axially spaced apart seal elements movable along said stem from a first position in which said seal elements bracket only a single one of said axially spaced apart apertures, said trigger assembly being manually movable axially to a second position in which said pair of seal elements bracket both of said pair of axially spaced apertures to communicate pressurized gas from one of said pair of apertures to the other of said pair of apertures and to said gas pressure piston.

2. The jet injection device of claim 1 wherein said trigger assembly further includes a trigger sleeve movable axially along said stem.

3. The jet injection device of claim 2 wherein said trigger sleeve carries said pair of seal elements in axially spaced apart relation, said trigger sleeve further cooperating with said stem member and with said pair of seal members to define an axially and radially extending annular chamber about said stem and between said pair of seal members.

4. The jet injection device of claim 3 wherein said stem member further defines a pair of axially extending bores aligned with one another and extending from opposite ends of said stem member toward but short of one another to not communicate internally of said stem member with one another, and wherein said pair of apertures comprises at least one cross bore extending outwardly from each of said pair of axially extending bores to open outwardly on an outer surface of said stem member.

5. The jet injection device of claim 3 wherein said source of pressurized gas includes a gas pressure cartridge with a penetrable diaphragm portion, and said jet injection device includes a penetrator member, and means for impaling said gas pressure cartridge at said diaphragm portion thereof upon said penetrator member to release pressurized gas from within said gas pressure cartridge, and to communicate this pressurized gas to said annular chamber.

6. The jet injection device of claim 1 wherein said gas pressure piston abuts against a movable ram member, said ram member including an elongate gear rack section formed along a side thereof, and a thumb wheel rotationally carried by said injector body and including a pinion gear drivingly engaged with said ram member gear rack section, whereby a user of said injection device may retract said injection piston to draw liquid medication into said injection cylinder by manual rotation of said thumb wheel preparatory to effecting a jet injection with said device.

7. The jet injection device of claim 6 wherein said ram carries a measurement indicating means for indicating to a user of said device the volume of liquid medication within said injection cylinder.

8. The jet injection device of claim 7 wherein said measurement indicating means includes said ram member carrying a pointer moving axially of said device in response to movement of said ram member, and a measurement scale carried on said device body and along which said pointer moves.

9. The jet injection device of claim 7 wherein said measurement indicating means includes said ram member carrying a binary scale moving along with said ram member, and means for responding to axial movement of said binary scale to indicate the volume of liquid medication in said injection cylinder, and to indicate digitally to a user of said device said volume of liquid medication.

10. The jet injection device of claim 7 wherein said measurement indicating means includes electronic means for responding to axial movement of said ram member, and for indicating digitally to a user of said device said volume of liquid medication in said injection cylinder.

11. A method of providing a jet injection device, said method comprising steps of:

providing a device body having a forward end;

providing an injection cylinder, and carrying said injection cylinder at a forward end of said device body, providing said injection cylinder with a cylinder bore in which an injection piston is movable to cooperatively define a variable-volume chamber for holding a dose of liquid medication;

providing a fine-dimension injection orifice in liquid flow communication with said variable-volume chamber to receive liquid medication, and discharging the liquid medication as a high velocity forceful jet for jet injection of medication upon forceful movement of said injection piston in said cylinder;

providing a power source in said device body for forcefully moving said piston in said cylinder in response to communication of gas pressure to a gas pressure piston, providing a source of gas pressure; and providing a trigger assembly for effecting communication of pressurized gas from said source to said gas pressure piston, configuring said trigger assembly to include a stem member with a pair of apertures spaced axially apart, and providing a pair of axially spaced apart seal elements movable along said stem from a first position in which said seal elements bracket only a single one of said axially spaced apart apertures, providing for said trigger assembly to be manually movable axially to a second position in which said pair of seal elements bracket both of said pair of axially spaced apertures to communicate pressurized gas from one of said pair of apertures to the other of said pair of apertures and to said gas pressure piston.

12. The method of claim 11 further including the step of providing said trigger assembly to further include a trigger sleeve movable axially along said stem.

13. The method of claim 12 further including the step of configuring said trigger sleeve to carry said pair of seal members in axially spaced apart relation, and utilizing said trigger sleeve to cooperate with said stem member and with said pair of seal elements to define an axially and radially extending annular chamber about said stem and between said pair of seal elements.

14. The method of claim 13 further including utilizing said stem member to define a pair of axially extending bores aligned with one another and extending from opposite ends of said stem member toward but short of one another to not communicate internally of said stem member with one another, and wherein said pair of apertures comprises at least one cross bore extending outwardly from each of said pair of axially extending bores to open outwardly on an outer surface of said stem member.

15. The method of claim 13 further including the step of including in said source of pressurized gas a gas pressure cartridge, and providing said gas pressure cartridge with a penetrable diaphragm portion, and providing said jet injection device with a penetrator member, providing said jet injection device further with means for impaling said gas pressure cartridge at said diaphragm portion thereof upon said penetrator member, and utilizing said impaling of said gas pressure cartridge to release pressurized gas from within said gas pressure cartridge and to communicate this pressurized gas to said annular chamber.

16. The method of claim 11 further including the steps of abutting said gas pressure piston against a movable ram member, and including on said ram member an elongate gear rack section formed along a side thereof, providing a thumb wheel rotationally carried by said injector body, and including with said thumb wheel a pinion gear drivingly engaged with said ram member gear rack section, and utilizing manual rotation of said thumb wheel to retract said injection piston to draw liquid medication into said injection cylinder preparatory to effecting a jet injection with said device.

17. The method of claim 16 further including the steps of carrying on said ram a measurement indicating means for indicating to a user of said device the volume of liquid medication within said injection cylinder.

18. The method of claim 17 further including the steps of carrying on said ram member a pointer moving axially of said device in response to movement of said ram member, and carrying on said device body a measurement scale along which said pointer moves.

19. The method of claim 17 wherein said measurement indicating means includes carrying on said ram member a binary scale moving along with said ram member, and also including means for responding to axial movement of said binary scale to indicate the volume of liquid medication in said injection cylinder so as to indicate digitally to a user of said device said volume of liquid medication.

20. A method of operating a jet injection device, said method comprising steps of:
   providing a device body having a forward end;
   providing an injection cylinder, and carrying said injection cylinder at a forward end of said device body, providing said injection cylinder with a cylinder bore in which an injection piston is movable to cooperatively define a variable-volume chamber for holding a dose of liquid medication;
   providing a fine-dimension injection orifice in liquid flow communication with said variable-volume chamber to receive liquid medication, and discharging the liquid medication as a high velocity forceful jet for jet injection of medication upon forceful movement of said injection piston in said cylinder;
   providing a power source in said device body for forcefully moving said piston in said cylinder in response to communication of gas pressure to a gas pressure piston, providing a source of gas pressure; and
   providing a stem member with a pair of axially extending bores extending from opposite ends of said stem member toward but short of one another, and a pair of apertures spaced axially apart and communicating respectively with one of said pair of bores,
   providing an axially spaced apart pair of seal elements slidably movable along said stem member between a first position in which said pair of seal elements bracket only a single one of said pair of apertures, and a second position in which said pair of seal elements bracket both of said pair of apertures;
   utilizing said pair of seal elements and a trigger sleeve carrying this pair of seal elements for axial movement along said stem member between said first and said second positions to cooperatively define an axially and radially extending annular chamber about said stem member at said apertures; and
   moving said trigger sleeve from a first of said first and second positions to a second of said positions to communicate pressurized gas from said source along one of said axially extending bores, radially outwardly from said one axially extending bore to said annular chamber via one of said pair of apertures, along said annular chamber between said pair of seal elements, radially inwardly via the other of said pair of apertures from said annular chamber to the other of said axially extending bores, and along said other axially extending bore to said gas pressure piston.

21. The method of claim 20 further including the step of including in said source of pressurized gas a gas pressure cartridge, and providing said gas pressure cartridge with a penetrable diaphragm portion, and providing said jet injection device with a penetrator member, providing said jet injection device further with means for impaling said gas pressure cartridge at said diaphragm portion thereof upon said penetrator member, and utilizing said impaling of said gas pressure cartridge to release pressurized gas from within said gas pressure cartridge and to communicate this pressurized gas to said annular chamber.

22. The method of claim 20 further including the steps of abutting said gas pressure piston against a movable ram member, and including on said ram member an elongate gear rack section formed along a side thereof, providing a thumb wheel rotationally carried by said injector body, and including with said thumb wheel a pinion gear drivingly engaged with said ram member gear rack section, and utilizing manual rotation of said thumb wheel to retract said injection piston to draw liquid medication into said injection cylinder preparatory to effecting a jet injection with said device.

23. The method of claim 22 further including the steps of carrying on said ram a measurement indicating means for indicating to a user of said device the volume of liquid medication within said injection cylinder.

24. The method of claim 23 further including the steps of carrying on said ram member a pointer moving axially of said device in response to movement of said ram member, and carrying on said device body a measurement scale along which said pointer moves.

25. The method of claim 23 wherein said measurement indicating means includes carrying on said ram member a binary scale moving along with said ram member, and also including means for responding to axial movement of said binary scale to indicate the volume of liquid medication in said injection cylinder so as to indicate digitally to a user of said device said volume of liquid medication.

26. A durable, refillable, needle-less let injection device comprising:
   a re-fillable drug injection cartridge including: a medication cylinder, an injection nozzle communication with said medication limier a drug-injection piston in a first position cooperating with said medication cylinder to define a variable-volume chamber of first selected size for receiving a dose of substantially incompressible liquid medication substantially filling said variable-volume chamber at said first size with substantially no ullage volume, said drug-injection piston having a recess thereon facing an open end of said medication cylinder, and said drug injection piston including means for removably retaining engagement thereof onto an injection ram, said drug injection cartridge at a forward end thereof including means for releasable coupling in sealing relation with a medication vial, and said drug injection cartridge at an aft end thereof including latching means for releasable engaging with a body of said device;

a hand piece body of said device, said body having a generally cylindrical elongate shape with an axially disposed opening at one end for receiving said drug injection cartridge, and a latching member movable between a first position in which said latching means of said medication cylinder is engaged to removably retain said medication cylinder at said body recess;

a source of pressurized gas including a hermetically sealed metallic gas capsule; penetrating means for penetrating said sealed gas capsule to release pressurized gas therefrom, and trigger means for selectively controlling flow of said pressurized gas from said gas capsule to a gas pressure piston and for controlling a application of force from said pressurized gas to said gas pressure piston and drug injection piston to move said drug injection piston from said first position to a second position in which said variable volume chamber is substantially reduced in volume, and said liquid medication is forcefully expelled from said chamber via said injection orifice to form a high-velocity injection jet, wherein said trigger means includes a trigger sleeve, a stem, and a pair of sealing members movable axially along said stem in response to axial movement of said trigger sleeve.

27. The jet injection device of claim 26 wherein said trigger sleeve carries said pair of seal members in axially spaced apart relation, said trigger sleeve further cooperating with said stem member and with said pair of seal members to define an axially and radially extending annular chamber about said stem and between said pair of seal members.

28. The jet injection device of claim 26 wherein said stem member further defines a pair of axially extending bores aligned with one another and extending from opposite ends of said stem member toward but short of one another to not communicate internally of said stem member with one another, said stem member also defining at least one cross bore extending outwardly from each of said pair of axially extending bores to open outwardly on an outer surface of said stem member.

29. The jet injection device of claim 28 wherein said gas pressure piston abuts against a movable ram member, said ram member including an elongate gear rack section formed along a side thereof, and a thumb wheel rotationally carried by said body and including a pinion gear drivingly engaged with said ram member gear rack section, whereby a user of said injection device may retract said injection piston to draw liquid medication into said injection cylinder by manual rotation of said thumb wheel preparatory to effecting a jet injection with said device.

30. The jet injection device of claim 29 wherein said ram carries a measurement indicating means for indicating to a user of said device the volume of liquid medication within said injection cylinder.

31. The jet injection device of claim 30 wherein said measurement indicating means includes said ram member carrying a pointer moving axially of said device in response to movement of said ram member, and a measurement scale carried on said device body and along which said pointer moves.

32. The jet injection device of claim 30 wherein said measurement indicating means includes said ram member carrying a binary scale moving along with said ram member, and means for responding to axial movement of said binary scale to indicate the volume of liquid medication in said injection cylinder, and to indicate digitally to a user of said device said volume of liquid medication.

* * * * *